United States Patent [19]

Dulapa et al.

[11] Patent Number: 4,492,119
[45] Date of Patent: Jan. 8, 1985

[54] ARTICULATED ARM ULTRASOUND IMAGING SYSTEMS

[75] Inventors: Mark J. Dulapa, Denver; William M. Glenn, Jr., Evergreen, both of Colo.

[73] Assignee: Technicare Corporation, Solon, Ohio

[21] Appl. No.: 463,426

[22] Filed: Feb. 3, 1983

[30] Foreign Application Priority Data

Oct. 1, 1982 [GB] United Kingdom ............... 8228094

[51] Int. Cl.³ .............................................. G01N 29/04
[52] U.S. Cl. ..................................................... 73/621
[58] Field of Search ......................... 73/620, 621, 633; 128/660; 364/559

[56] References Cited

U.S. PATENT DOCUMENTS

| 3,924,452 | 12/1975 | Meyer et al. | 73/621 |
| 3,944,798 | 3/1976 | Eaton | 73/621 |
| 4,014,207 | 3/1977 | Meyer et al. | 73/621 |
| 4,244,227 | 1/1981 | Rudolph et al. | 73/633 |

Primary Examiner—Stephen A. Kreitman
Attorney, Agent, or Firm—W. Brinton Yorks, Jr.

[57] ABSTRACT

An ultrasound imaging system is provided having an articulated arm for holding a transducer. Signals representative of the angular position of the arm joints are scaled up to a voltage range over which the restricted range of movement of each joint is distributed. The scaled signals are combined to produce a plurality of combined angular signals, which then may be digitized and used to compute the X-Y position of the transducer.

10 Claims, 5 Drawing Figures

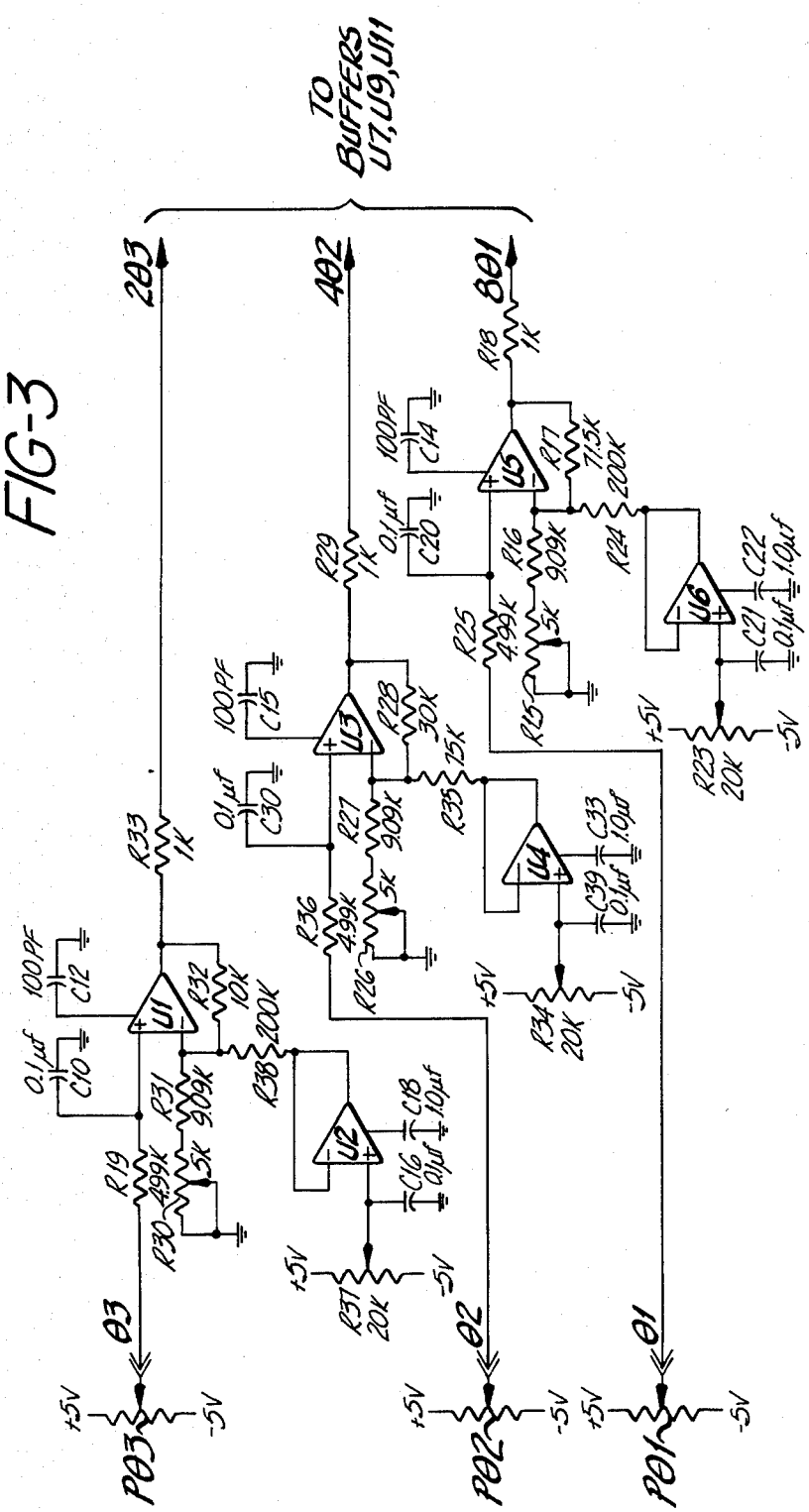

ARTICULATED ARM ULTRASOUND IMAGING SYSTEMS

This invention relates to ultrasound imaging systems, and more particularly to such systems which employ multiple segment, articulated arms for providing positional information.

One well-known type of ultrasound imaging system is the static B-scan system. A commercially available system is the EDP 1200 Diagnostic Ultrasound System, manufactured by Technicare Corporation. Systems of this type typically involve a multiple segment (e.g. three) articulated arm, with a transducer attached at the end. The angular positions of the respective segments are monitored and encoded, typically by potentiometers at the respective joints, whereby there is always available precise positional information concerning the transducer, and hence its relation to the patient being examined. Through mechanical manipulation of the transducer, images of high line density over a large field of view can be generated. Typically, these static images provide hard copy records of the highest image quality available in the ultrasound modality.

U.S. Pat. No. 4,381,787 issued to Charles F. Hottinger and entitled "ULTRASOUND IMAGING SYSTEM COMBINING STATIC B-SCAN AND REAL-TIME SECTOR SCANNING CAPABILITY" describes a processor for the signals developed by the potentiometers of a three-segment B-scan arm. In the processor there described, angular positional information from the respective joints of the arm is coupled to a gain and offset amplifier to appropriately scale the voltages developed by the potentiometers. Next, these three angular voltage quantities are coupled to an x-y converter, which utilizes trigonometric relationships to convert the three angular quantities, $\theta 1$, $\theta 2$, and $\theta 3$, to x and y positional and directional information of the terminus of the multisegmented arm. Four separate values, including x and y position and x and y directions, are coupled to an analog multiplexer, which converts the four parallel quantities into a serial format, and is capable of scaling the quantities to provide an optional "zoom" feature. The serialized analog data from the multiplexer is coupled to an analog multiplier, where field of view scaling data is combined with the x and y slope and x and y position values. The data from the multiplexer, still in analog form, is coupled to a sample and hold unit and thereupon to an analog to digital converter which reads each voltage value from the sample and hold unit to produce digital words representing the instantaneous x position, y position, x slope, and y slope values. These position values represent the position of a transducer of a scan head coupled to the terminus of the B-scan arm.

Analog positional information processors of the type just described generally employ numerous potentiometers for adjustment of voltage parameters within the system. Accordingly, it would be desirable to perform much of this processing in digital data form to eliminate the need for adjustment of analog controls. However, the partitioning between analog and digital processing, that is, the point in the signal paths at which analog values are converted to digital values, must be carefully considered so as to minimize system hardware requirements while maintaining desired system accuracy.

In particular, it has been found by the present inventor that digitizing at the outset of processing, such as immediately following the B-scan arm joint potentiometers, can lead to serious quantization errors. These quantization errors will mainfest themselves as jagged edges on the scan image and sawtooth patterns along the skin line of the image.

In accordance with the principles of the present invention, the angular position-representative voltages produced by the potentiometers of B-scan arm joints are offset and scaled as a function of the permissible angular travel of the respective joints. This permits the angles of interest to be quantized over the full scale of the analog to digital converter. Least significant bit quantization errors are further reduced by combining angular voltage values prior to digitization. The offset, scaled and combined angular-representative voltage values are then converted to digital values, resulting in accurate position-representative digital processing.

In the drawings:

FIG. 3 illustrates scaling circuitry associated with the B-scan arm of FIG. 2.

Figure 1:
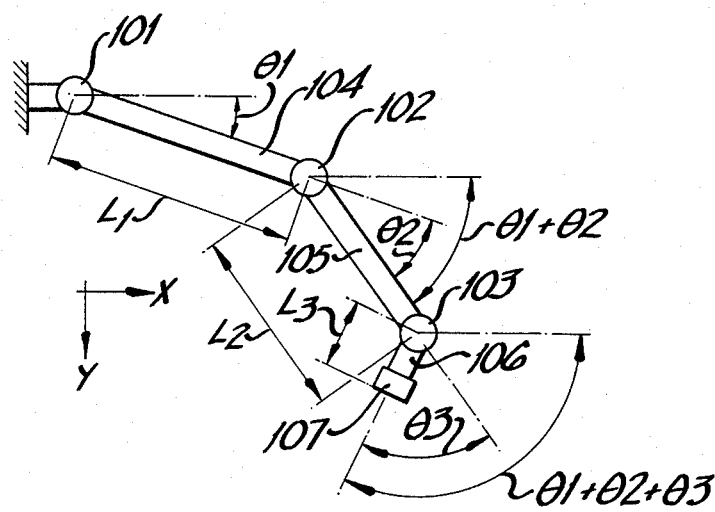
FIG. 1 illustrates a triple jointed B-scan arm used for positional location in B-scan systems.

Referring to FIG. 1, there is shown symbolically a multisegmented B-scan arm as described in the aforementioned U.S. Pat. No. 4,381,787. The arm of FIG. 1 includes three segments 104, 105 and 106, coupled to a fixed reference (not shown in detail) at a top joint 101, and coupled to one another at joints 102 and 103. A bracket 107, shown symbolically in FIG. 1, holds a transducer, which in turn engages the patient in a pulse-echo exchange of sonic energy. The articulated arm of FIG. 1 has means (typically potentiometer circuits) located at each joint 101, 102, and 103 for determining the respective angles $\theta 1$, $\theta 2$, and $\theta 3$. Voltages from the potentiometers thus correspond to the positions of arms 104, 105, and 106 with respect to each other, thereby identifying the position and orientation of the outermost terminus 107 with respect to the positionally stationary joint 101. It will be appreciated from the principles of trigonometry that the location of terminus 107 relative to joint 101 may be resolved into x and y components, the x component or position being a function of the lengths L1, L2 and L3 of the arms 104, 105, and 106, respectively, and the cosines of the angles $\theta 1$, $(\theta 1+\theta 2)$, and $(\theta 1+\theta 2+\theta 3)$. Likewise, the y component or location of point 107 relative to point 101 will be similarly obtained as a function of the sines of the various angles.

Mathematically, the locations of the x and y positional components of point 107 components are stated as follows:

$$P(x) = L1 \cos \theta 1 + L2 \cos (\theta 1 + \theta 2) + L3 \cos (\theta 1 + \theta 2 + \theta 3)$$

$$P(y) = L1 \sin \theta 1 + L2 \sin (\theta 1 + \theta 2) + L3 \sin (\theta 1 + \theta 2 + \theta 3)$$

It will also be apparent that the slope of direction of an ultrasound beam from the transducer at point 107 may be determined based upon the angle $(\theta 1+\theta 2+\theta 3)$, the x slope being a function of the cosine of that angle, and the y slope being a function of the sine of that angle.

Figure 2:
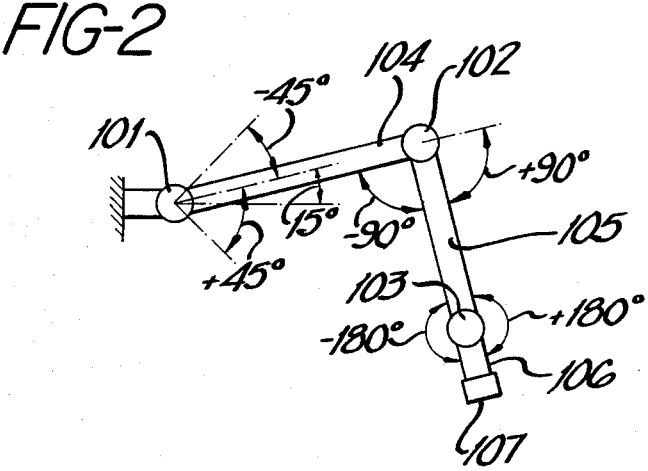
FIG. 2 illustrates a triple jointed B-scan arm arranged in accordance with the principles of the present invention.

Referring to FIG. 2, an articulated ultrasound B-scan arm, constructed in accordance with the principles of the present invention, is shown in its nominal detent position. A position-sensing potentiometer P$\theta$1, P$\theta$2, P$\theta$3 is associated with each of joints 101, 102, and 103, respectively. Each potentiometer is coupled between +5 V and −5 V supplies, as shown in FIG. 3. When the upper arm segment 104 is positioned 15° above horizontal as shown in FIG. 2, the potentiometer P$\theta$1 is at its center position, producing a 0 volt output. The potentiometer output voltage would vary between +5 volts and −5 volts if the arm segment were moved +180° and −180° from its nominal position. However, joint 101 permits movement of only ±45 from the nominal zero volt position. Hence, the wiper of potentiometer P$\theta$1 will not traverse its full possible range.

Arm segment 105 is normally located at a 90° relationship with respect to the nominal position of arm segment 104 in its zero volt output position. Arm segment 105 is capable of movement of ±90° with respect to this nominal position. Arm segment 106 is in line with arm segment 105, and is capable of virtually 360 of motion (±180°) by operation of joint 103.

In order to provide a high degree of accuracy of arm positioning information, the present invention takes cognizance of the fact that motion by joints 101 and 102 is restricted to less than 360°. Accordingly, the voltages of the three arm potentiometers are respectively scaled up to a voltage range of ±10 volts by the circuitry of FIG. 3, with the permissible rotation range of each joint being distributed over the full voltage range. In the case of potentiometer P$\theta$3 of joint 103, its output voltage can vary over the full ±5 volt range of the potentiometer. In FIG. 3, the P$\theta$3 voltage is amplified by two by amplifier U1, producing an output 2$\theta$3 over a voltage range of ±10 volts. The permissible ±90° of rotation of joint 102 means that the output voltage of potentiometer P$\theta$2 is confined to limits of ±2.5 volts. Thus, amplifier U3 exhibits a gain of four to produce an output voltage 4$\theta$2 over a range of ±10 volts. Similarly, joint 101 is constrained to motion between limits of ±45°, thereby causing potentiometer P$\theta$1 to have an output voltage range of ±1.25 volts. The output voltage of potentiometer P$\theta$1 is therefore amplified by a gain of eight by amplifier U5 to produce an output signal 8$\theta$1 with a range of ±10 volts. Each amplifier of FIG. 3 includes a trimmer (R15, R26, R30) for precise adjustment of amplifier gain, and a voltage offset amplifier (U2, U4, U6) to permit compensation for voltage offsets in the potentiometer and arm assembly.

Figure 4A:
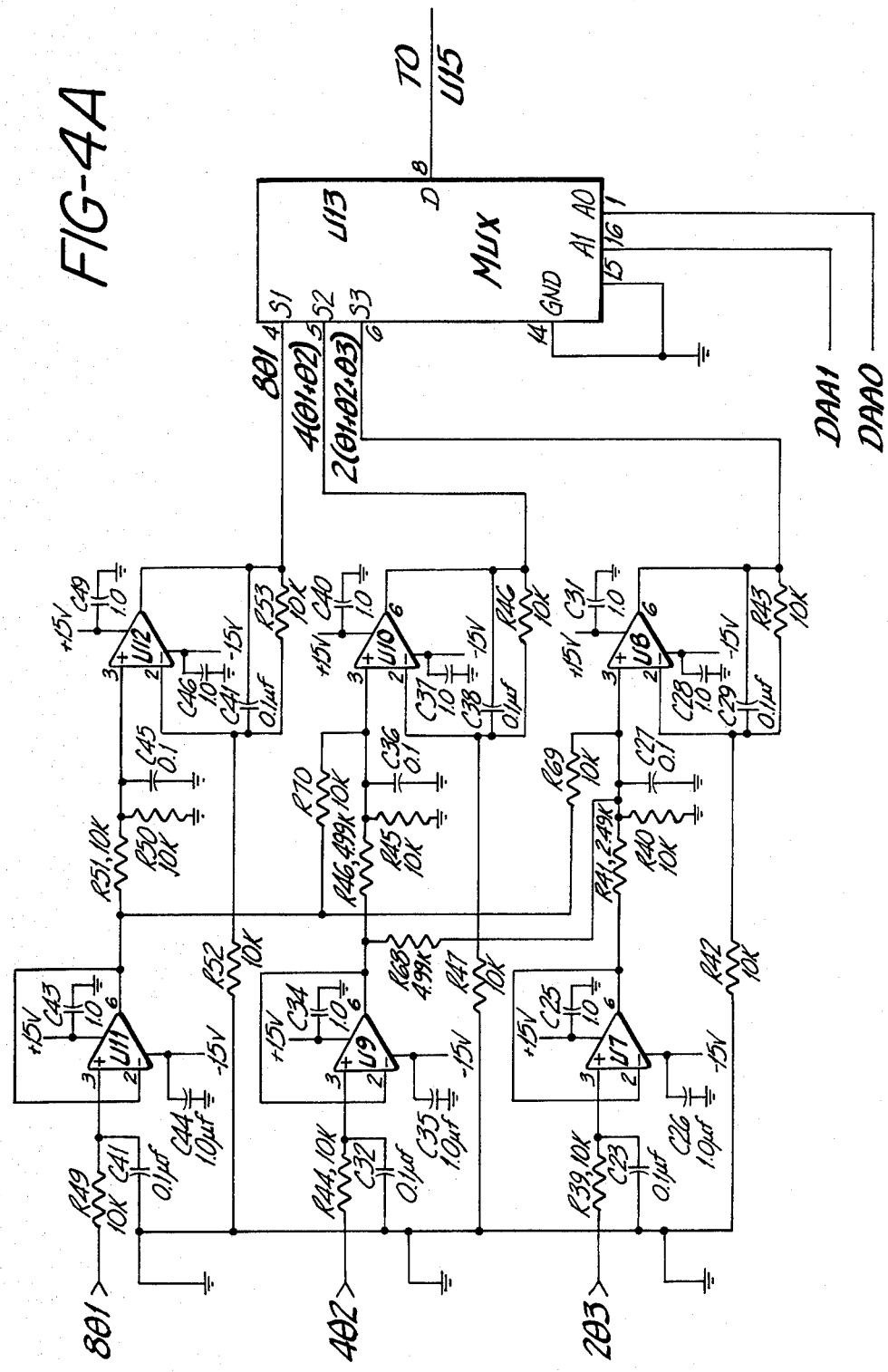
FIGS. 4A and 4B illustrate angular information processing circuitry utilized in conjunction with the arrangements of FIGS. 2 and 3.
Figure 4B:
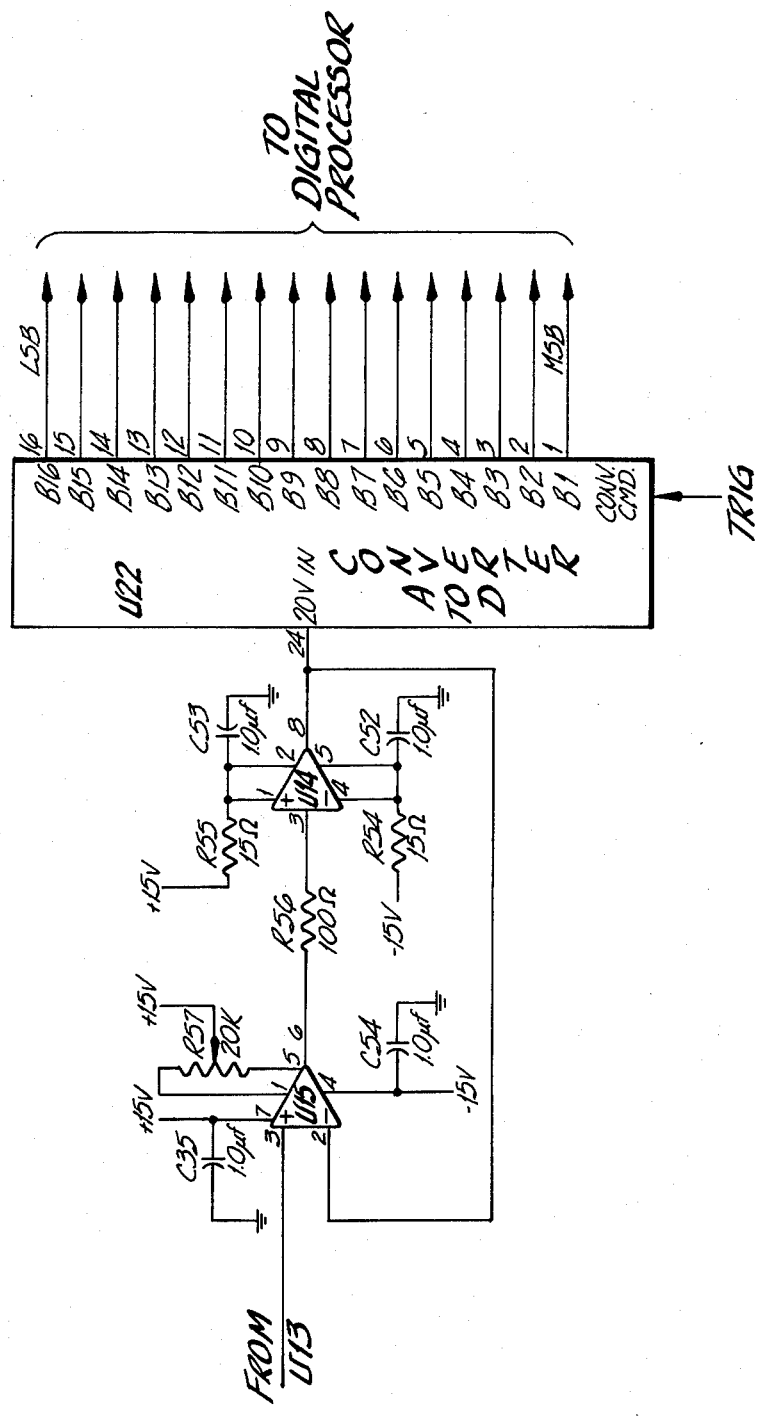

The scaled voltage values 2$\theta$3, 4$\theta$2 and 8$\theta$1 are applied to inputs of the angular information processing circuitry of FIGS. 4A and 4B. In the arrangement of FIG. 4A, the angular voltage values are first rescaled and combined in the forms in which they will be used by the sine and cosine formulae given above. Each expression is seen to contain a $\theta$1 term, a ($\theta$1+$\theta$2) term, and a ($\theta$1+$\theta$2+$\theta$3) term. To create angular voltage values in these forms, each scaled voltage value is first applied to a buffer amplifier U7, U9, and U11, respectively. The 8$\theta$1 output signal of buffer U11 is dropped across resistor R50 and R51 to produce a voltage of the form 8$\theta$1/2 at the positive input of amplifier U12. Amplifier U12 exhibits a voltage gain of two, thereby producing an output signal of the form 8$\theta$1 which is applied to an input of a multiplexer U13.

Buffer amplifier U9 produces an output signal of the form 4$\theta$2, which is combined with the 8$\theta$1 signal of buffer U11 by the resistive combining network R45, R46, R70. It is seen in this example that the 8$\theta$1 signal is coupled by way of a 10K resistor R70, whereas the 4$\theta$2 signal is coupled by way of a 4.99K resistor R46. Using the resistor values in a superposition calculation, it can be seen that the signal at the positive input of amplifier U10 is of the form (2$\theta$1+2$\theta$2). This signal is then buffered and amplified by amplifier U10, which exhibits a gain of two, to produce a signal of the form 4 ($\theta$1+$\theta$2). The combining network thus scales the 8$\theta$1 voltage down to a comparable voltage range as that of the 4$\theta$2 voltage. The output signal of amplifier U10 is applied to a second input of the multiplexer U13.

Similarly, signals 8$\theta$1, 4$\theta$2, and 2$\theta$3 are scaled and combined at the positive input of an amplifier U8 by a resistive combining network, including resistors R40, R41, R68, and R69. This resistive combining network scales the 8$\theta$1 and 4$\theta$2 signals down to the range of the 2$\theta$3 signal. By superposition calculations using the illustrated resistor values, it can be seen that the input signal to amplifier U8 is of the form ($\theta$1+$\theta$2+$\theta$3). This signal is amplified by two by amplifier U8, which applies a signal of the form 2 ($\theta$1+$\theta$2+$\theta$3) to a third input of the multiplexer U13.

The multiplexer U13 is controlled by signals DAA0 and DAA1 to sequentially conduct the three combined angular voltages to the output of the multiplexer. The angular voltage values may be modified by the gain of an amplifier U15, shown in FIG. 4B by which compensation is made for any constant nonlinearities in the system. The voltage values are then applied to a driver amplifier U14, which applies the angular voltage values to the input of an analog to digital converter U22. The analog to digital converter converts each of the three angular voltage values to a sixteen bit digital word in response to a convert command signal TRIG. The digital words are then coupled to a digital processor (not shown) which uses a look-up table responsive to the combined angular signals to perform the trigonometric calculations necessary to determine the x and y positions of the ultrasonic probe on terminus 107.

The embodiment of the present invention shown in FIGS. 3, 4A, and 4B provides good resolution of the angular coordinates of the articulated arm, since the potentiometer outputs are immediately converted to ranges which utilize the full dynamic range of the system's voltage supply to quantize the respective angular ranges of the arm segments. The converted angular voltage values are then combined with proper scaling to produce three voltges representative of the expressions required by the trigonometric look-up table in the processor. By digitally converting the analog values after this combining has been done in the analog domain, quantization errors resulting from digital signal combining are prevented. Highly accurate positional information from the articulated arm is thereby provided.

What is claimed is:

1. In an ultrasonic diagnostic imaging system, including an articulated arm for mounting an ultrasonic scanner, said arm including a plurality of joints, at least two of which exhibit respectively different permitted angular ranges of movement; apparatus for processing signals indicative of the arm position comprising:

means, associated with said joints, for providing analog output signals representative of the angular position of said joints;

means, responsive to said angular position output signals, for producing a plurality of scaled analog output signals over a common dynamic range corresponding to the respective permitted angular ranges of movement of said arm joints;

means for proportionately combining ones of said scaled output signals to provide a plurality of combined angular representative analog signals; and means for digitizing said combined angular representative analog signals.

2. The arrangement of claim 1, wherein said means associated with said joints comprises potentiometers.

3. The arrangement of claim 2, wherein ones of said joints are restricted to different ranges of angular movement, and wherein said scaled output signal producing means comprises a plurality of amplifiers responsive to ones of said angular position output signals, respectively, and having respective gains for translating the dynamic range of said angular position output signals over the dynamic range of said amplifiers.

4. In an ultrasonic diagnostic imaging system, including an articulated arm for mounting an ultrasonic scanner, said arm including a plurality of joints; apparatus for processing signals indicative of the arm position comprising:

means, associated with said joints, for providing output signals representative of the angular position of said joints;

means, responsive to said angular position output signals, for producing a plurality of scaled output signals over a dynamic range corresponding to the respective permitted angular ranges of movement of said arm joints;

means for proportionately combining ones of said scaled output signals to provide a plurality of combined angular representative signals; and means for digitizing said combined angular representative signals, wherein said means associated with said joints comprises potentiometers, wherein ones of said joints are restricted to different ranges of angular movement, and wherein said scaled output signal producing means comprises a plurality of amplifiers responsive to ones of said angular position output signals, respectively, and having respective gains for translating the dynamic range of said angular position output signals over the dynamic range of said amplifiers, and wherein said proportionately combining means comprises a plurality of resistive summing networks.

5. The arrangement of claim 4, wherein said proportionately combining means further comprises means for scaling combined signals to a common voltage range.

6. The arrangement of claim 5, further comprising a multiplexer for serially transmitting said combined angular representative signals to said digitizing means.

7. In an ultrasonic diagnostic imaging system, including an articulated arm for mounting an ultrasonic scanner, said arm including a plurality of joints and means for providing analog signals representative of the angular position of said joints; signal processing apparatus comprising:

means for combining ones of said angular position representative analog signals to produce combined angular representative analog signals;

means for digitizing said combined angular representative analog signals; and a digital processor, responsive to said digitized combined angular representative signals, for calculating the position of said ultrasonic scanner.

8. The arrangement of claim 7, wherein said combining means comprises a plurality of resistive summing networks.

9. In an ultrasonic diagnostic imaging system, including an articulated arm for mounting an ultrasonic scanner, said arm including a plurality of joints and means for providing analog signals representative of the angular position of said joints; signal processing apparatus comprising:

means for combining ones of said angular position representative analog signals to produce combined angular representative analog signals;

means for digitizing said combined angular representative analog signals; and a digital processor, responsive to said digitized combined angular representative signals, for calculating the position of said ultrasonic scanner, wherein said combining means comprises a plurality of resistive summing networks, and wherein said combining means further comprises:

a plurality of buffer amplifiers having respective inputs responsive to respective ones of said angular position representative analog signals and outputs coupled to said summing networks; and a plurality of output amplifiers having respective inputs coupled to ones of said summing networks, and outputs coupled to said digitizing means.

10. The arrangement of claim 9, further comprising a multiplexer having inputs coupled to respective outputs of said output amplifiers and an output coupled to said digitizing means.

* * * * *